United States Patent
Marquette (10) Patent No.: US 10,451,535 B2
(45) Date of Patent: Oct. 22, 2019

(54) TIMING AND/OR PHASE ADJUSTMENT OF THE SEPARATION AND/OR CHARGING OF DROPS FROM A FLUID STREAM IN A FLOW CYTOMETER

(71) Applicant: Bio-Rad Laboratories, Inc., Hercules, CA (US)

(72) Inventor: Edward Marquette, Oakland, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 76 days.

(21) Appl. No.: 15/883,229

(22) Filed: Jan. 30, 2018

(65) Prior Publication Data

US 2018/0156712 A1 Jun. 7, 2018

Related U.S. Application Data

(62) Division of application No. 14/460,580, filed on Aug. 15, 2014, now Pat. No. 10,126,225.

(Continued)

(51) Int. Cl.
*G01N 15/14* (2006.01)
*G01N 15/10* (2006.01)
*G01R 5/28* (2006.01)

(52) U.S. Cl.
CPC ..... *G01N 15/1404* (2013.01); *G01N 15/1012* (2013.01); *G01N 15/1427* (2013.01);
(Continued)

(58) Field of Classification Search
CPC ........... G01N 15/1404; G01N 15/1527; G01N 15/1012; G01N 2015/149; G01N 2015/1406; G01R 5/28
(Continued)

(56) References Cited

U.S. PATENT DOCUMENTS

| | | | | |
|---|---|---|---|---|
| 2,756,388 A | * | 7/1956 | McLean | G01R 5/28 324/453 |
| 3,297,887 A | | 1/1967 | Marks | |

(Continued)

FOREIGN PATENT DOCUMENTS

| | | |
|---|---|---|
| CN | 101887003 | 11/2010 |
| CN | 102830053 | 12/2012 |

(Continued)

OTHER PUBLICATIONS

Chinese First Office Action dated Mar. 13, 2018, in Application No. 201480052117.2.

(Continued)

*Primary Examiner* — Jill A Warden
*Assistant Examiner* — Brittany I Fisher
(74) *Attorney, Agent, or Firm* — Weaver Austin Villeneuve & Sampson LLP (57) ABSTRACT

Disclosed is a system for setting the timing or phase of the separation of droplets from a fluid stream in a flow cytometer, or the timing or phase of a charge pulse generator, based upon the collected charge of charged droplets. In one embodiment, a conductive mesh can be used to collect the charged droplets that are either deflected or not deflected by the deflection plates. In another embodiment, the charge can be collected from metal plates in the waste collection device. In addition, a defanning device is disclosed that allows substantially uniform deflection of charged cells.

12 Claims, 9 Drawing Sheets

Related U.S. Application Data (60) Provisional application No. 61/866,639, filed on Aug. 16, 2013.

(52) U.S. Cl.
CPC ............... *G01N 2015/1406* (2013.01); *G01N 2015/149* (2013.01); *G01R 5/28* (2013.01)

(58) Field of Classification Search
USPC ........................................................ 422/508
See application file for complete search history.

(56) References Cited

U.S. PATENT DOCUMENTS

| | | | |
|---|---|---|---|
| 3,380,584 A | | 4/1968 | Fulwyler |
| 3,596,276 A | | 7/1971 | Lovelady et al. |
| 3,761,941 A | | 9/1973 | Robertson |
| 3,963,606 A | | 6/1976 | Hogg |
| 4,012,745 A | | 3/1977 | Brown et al. |
| 4,284,496 A | * | 8/1981 | Newton .................. G01N 1/28 209/127.1 |
| 4,318,480 A | | 3/1982 | Lombardo et al. |
| 4,616,234 A | | 10/1986 | Wint |
| 4,667,830 A | | 5/1987 | Nozaki, Jr. et al. |
| 4,928,115 A | * | 5/1990 | Fagerquist ................. B41J 2/01 347/108 |
| 4,994,821 A | * | 2/1991 | Fagerquist ............... B41J 2/125 347/81 |
| 5,150,036 A | * | 9/1992 | Pourprix ............ G01N 15/0656 324/601 |
| 5,158,889 A | * | 10/1992 | Hirako ................... C12M 47/04 250/461.2 |
| 5,641,457 A | | 6/1997 | Vardenega et al. |
| 5,643,796 A | | 7/1997 | Van den Engh et al. |
| 5,652,598 A | | 7/1997 | Campbell et al. |
| 5,700,692 A | | 12/1997 | Sweet |
| 6,079,836 A | | 6/2000 | Burr et al. |
| 6,221,136 B1 | | 4/2001 | Liu et al. |
| 6,248,590 B1 | | 6/2001 | Malachowski |
| 6,372,506 B1 | | 4/2002 | Norton |
| 6,589,792 B1 | | 7/2003 | Malachowski |
| 6,941,005 B2 | | 9/2005 | Lary et al. |
| 7,294,249 B2 | * | 11/2007 | Gawad .............. B01L 3/502761 204/547 |
| 8,603,396 B2 | | 12/2013 | Sharpe et al. |
| 2005/0030534 A1 | | 2/2005 | Oldham et al. |
| 2005/0112541 A1 | | 5/2005 | Durack et al. |
| 2006/0170912 A1 | | 8/2006 | Mueth et al. |
| 2007/0117086 A1 | | 5/2007 | Evans et al. |
| 2009/0189932 A1 | | 7/2009 | Lee et al. |
| 2009/0233057 A1 | * | 9/2009 | Aksay ........................ B41J 2/06 428/195.1 |
| 2012/0202237 A1 | | 8/2012 | Sedoglavich et al. |
| 2013/0015257 A1 | | 1/2013 | Kalra et al. |
| 2013/0240752 A1 | * | 9/2013 | Ma .......................... B03C 3/025 250/397 |

FOREIGN PATENT DOCUMENTS

| | | |
|---|---|---|
| CN | 103180713 | 6/2013 |
| WO | 2011/0112656 | 9/2011 |
| WO | 2012/106294 | 8/2012 |
| WO | 2012/0148584 | 11/2012 |
| WO | 2015/023916 | 2/2015 |

OTHER PUBLICATIONS

International Search Report and Written Opinion dated Dec. 18, 2014, in Application No. PCT/US2014/051202.
European Invitation pursuant to Rule 62a(1) dated Feb. 7, 2017, in Application No. 14836266.8.
Extended European Search Report dated Jun. 21, 2017, in Application No. 14836266.8.

* cited by examiner

TIMING AND/OR PHASE ADJUSTMENT OF THE SEPARATION AND/OR CHARGING OF DROPS FROM A FLUID STREAM IN A FLOW CYTOMETER

CROSS REFERENCE TO RELATED APPLICATIONS

This application is a divisional application under 35 U.S.C. § 120 of U.S. patent application Ser. No. 14/460,580, filed Aug. 15, 2014, and titled "TIMING AND/OR PHASE ADJUSTMENT OF THE SEPARATION AND/OR CHARGING OF DROPS FROM A FLUID STREAM IN A FLOW CYTOMETER," which is hereby incorporated herein by reference in its entirety and which also claims benefit of priority under 35 U.S.C. § 119(e) to U.S. Provisional Patent Application No. 61/866,639, filed Aug. 16, 2013 and titled "TIMING AND/OR PHASE ADJUSTMENT OF THE SEPARATION AND/OR CHARGING OF DROPS FROM A FLUID STREAM IN A FLOW CYTOMETER."

BACKGROUND

Flow cytometers are useful devices for analyzing and sorting various types of particles in fluid streams. These cells and particles may be biological or physical samples that are collected for analysis and/or separation. The sample is mixed with a sheath fluid for transporting the particles through the flow cytometer. The particles may comprise biological cells, calibration beads, physical sample particles, or other particles of interest, which are collectively referred to herein as "particles." Sorting and analysis of these particles can provide valuable information to both researchers and clinicians. In addition, sorted particles can be used for various purposes to achieve a wide variety of desired results.

SUMMARY

An embodiment of the invention may comprise a method of adjusting the timing or phase of separation of droplets from a fluid stream of sheath fluid in a flow cytometer comprising: charging the droplets with a charge pulse signal while the droplets are separating from the fluid stream to create a stream of charged droplets; adjusting the timing or phase for separation of the droplets from the fluid stream; collecting charges from the charged droplets for a plurality of timing or phase settings; measuring the charges collected from the charged droplets for the timing or phase setting to create a plurality of collected charged droplet signals; determining a collected charged droplet signal of the plurality of collected charged droplet signal that has the greatest magnitude; operating the flow cytometer with a timing or phase setting of the plurality of timing or phase settings that corresponds to the collected charge droplet signal that has the greatest magnitude.

An embodiment of the invention may further comprise a system for adjusting the timing or phase of separation of droplets formed from a fluid stream of a sheath fluid in a flow cytometer comprising: a nozzle that forms the fluid stream; a charge pulse generator that is connected to the nozzle that generates a charge pulse that charges the fluid stream through the nozzle as the droplets separate from the fluid stream to create charged droplets; a charge collector disposed to receive the charged droplets and accumulate a charge from the charged droplets; an electrometer connected to the charge collector that detects the accumulated charge and generates an accumulated charge signal; a controller that adjusts the timing or phase in response to the accumulated charge signal.

An embodiment of the invention may further comprise a method of adjusting the timing or phase of a charge signal for charging droplets from a fluid stream of sheath fluid in a flow cytometer comprising: charging the droplets with a charge pulse signal while the droplets are separating from the fluid stream to create a stream of charged droplets; adjusting the timing or phase of the charge signal; collecting charges from the charged droplets for a plurality of timing or phase settings; measuring the charges collected from the charged droplets for the timing or phase setting to create a plurality of collected charged droplet signals; determining a collected charged droplet signal of the plurality of collected charged droplet signal that has the greatest magnitude; operating the flow cytometer with a timing or phase setting of the plurality of timing or phase settings that corresponds to the collected charge droplet signal that has the greatest magnitude.

An embodiment of the invention may further comprise a system for adjusting the timing or phase of a charge pulse signal for charging droplets formed from a fluid stream of a sheath fluid in a flow cytometer comprising: a nozzle that forms the fluid stream; a charge pulse generator that is connected to the nozzle that generates a charge pulse that charges the fluid stream through the nozzle as the droplets separate from the fluid stream to create charged droplets; a charge collector disposed to receive the charged droplets and accumulate a charge from the charged droplets; an electrometer connected to the charge collector that detects the accumulated charge and generates an accumulated charge signal; a controller that adjusts the timing or phase of the charge pulse signal in response to the accumulated charge signal.

An embodiment of the invention may further comprise a method of adjusting the amplitude of a charge signal that is applied to droplets formed from a fluid stream in a flow cytometer to create a substantially uniform charge on the droplets in a fluid stream comprising: generating a plurality of charge series of the droplets; identifying the droplets that have been affected by electric fields of preceding droplets as affected droplets for each of the charge series; separating the affected droplets in a static electric field; collecting the affected droplets in a conductive collector; detecting an accumulated charge in the conductive collector of the affected droplets to obtain an accumulated charge magnitude for each charge series of the plurality of charge series; using the accumulated charge magnitude of the affected droplets to adjust the amplitude of the charge signal for droplets that exist in each charge series of the plurality of charge series.

An embodiment of the invention may further comprise a system for adjusting a charge amplitude of a charge pulse signal that is applied to droplets formed from a fluid stream in a flow cytometer to create a substantially uniform charge on the droplets comprising: a charge pulse generator that generates the charge pulse signal in response to a control signal, that has a charge magnitude that charges droplets just prior to separation from the fluid stream to obtain charged droplets; at least one conductive collector that collects the charged droplets and accumulates a charge having a charge magnitude; an electrometer connected to the at least one conductive collector that detects the charge magnitude and generates a charge magnitude signal; a processor that receives the charge magnitude signal and generates the control signal, the control signal producing a plurality of charge series of the droplets that produces affected droplets that have a charge that has been affected by electric fields of preceding droplets and non-affected droplets that have not been affected by electric fields of preceding droplets, and compares the charge magnitude signal for the affected droplets and the non-affected droplets for the plurality of charge series to alter the charge magnitude of the control signal, which charges the droplets to a uniform magnitude during operation of the flow cytometer.

DETAILED DESCRIPTION OF THE EMBODIMENTS

Figure 1:
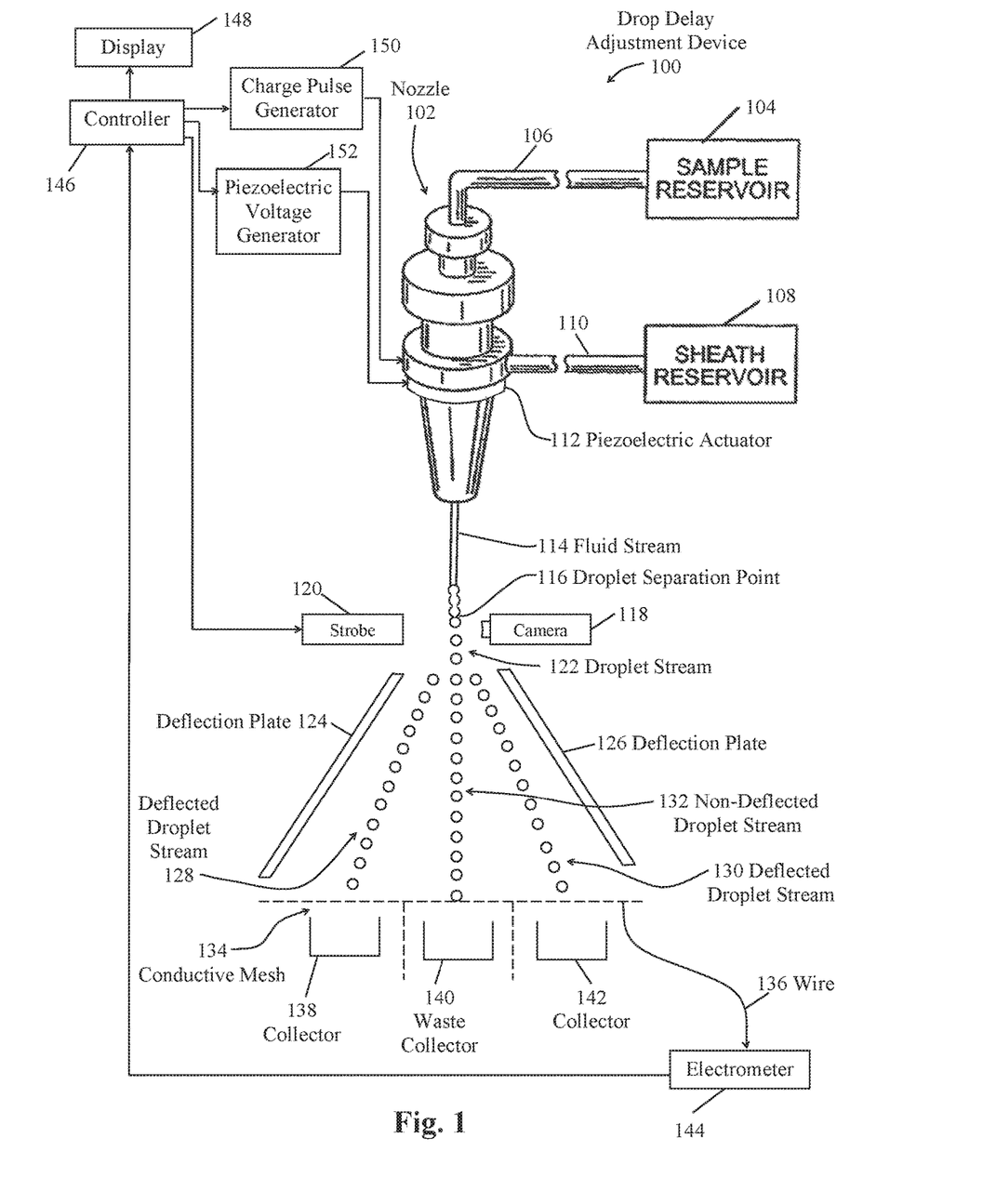
FIG. 1 is a schematic block diagram illustrating an embodiment of a timing and phase adjustment system for the separation of drops from a fluid stream in a flow cytometer.

FIG. 1 is a schematic block diagram illustrating an embodiment of the timing and phase adjustment system 100 for the separation of drops from a fluid stream in a flow cytometer. As illustrated in FIG. 1, sample reservoir 104 is connected to nozzle 102 by conduit 106. Sample reservoir 104 provides sample particles to be separated by the flow cytometer illustrated in FIG. 1. Sheath reservoir 108 is also connected to the nozzle 102 and supplies sheath fluid via conduit 110 to the nozzle 102. Various processes for maintaining a substantially constant pressure of sheath fluid are disclosed in U.S. Provisional Patent Application Ser. No. 61/659,528, filed Jun. 14, 2012, by Daniel N. Fox and Nathan M. Gaskill-Fox, entitled "Flow Rate Balance, Dynamically Adjustable Sheath Delivery System for Flow Cytometry," which is specifically incorporated herein by reference, for all that it discloses and teaches. The sheath fluid supplied by conduit 110 is combined with the sample fluid in the nozzle 102 and flows downwardly out of the nozzle 102 to form fluid stream 114. The nozzle includes a piezoelectric actuator 112, which generates vibrations in the fluid stream 114 to cause the fluid stream 114 to break into droplets at the droplet separation point 116. The piezoelectric actuator 112 operates in response to a piezoelectric voltage generator 152 that is disclosed in more detail with respect to FIG. 2.

The manner in which a flow cytometer, such as the flow cytometer illustrated in FIG. 1, separates droplets is by applying a charge pulse to a droplet, so that the droplet can be deflected by deflection plates 124, 126 that are charged with positive and negative voltages. The droplets become charged by applying a charge pulse from charge pulse generator 150 to the stream 114 during, but not after, prior to the time that droplets become separated from the fluid stream 114 at droplet separation point 116. In that manner, the fluid stream 114 becomes charged and the charge on the fluid stream 114 is transferred to the droplets in the droplet stream 122 when the droplets separate from the fluid stream 114. If the fluid stream 114 is charged too early, the charge on the fluid stream 114 will fade and the droplets in the droplet stream 122 will only have a small charge, or no charge. If the charge pulse is applied too late, i.e., after the droplet separates from the fluid stream 114, the droplet will have no charge, since the droplet was not connected to the stream when the charge is applied to the fluid stream 114.

Accordingly, to properly charge droplets in the droplet stream 122 with a charge pulse, the charge pulse must be applied to the fluid stream 114 while, but not before, the droplet separates from fluid stream 114. The intensity and frequency of the piezoelectric actuator 112, and the timing of the charge pulse generated by the charge pulse generator 150, can be adjusted so that the charge pulse is applied to fluid stream 114 at the proper time. The piezoelectric generator 152 operates in response to control signal 157 generated by controller 146.

As also illustrated in FIG. 1, the charge pulse generator 150 and the piezoelectric voltage generator 152 are controlled by the controller 146. Controller 146 can vary the operational parameters of the piezoelectric voltage generator 112 to vary the intensity and frequency of the piezoelectric actuator 112 and thereby change the timing and phase of the separation of the droplet from the fluid stream. In addition, the location of the droplet separation point 116, which is the point where the droplets in the droplet stream 122 separate from the fluid stream 114, may also change. The charge pulse generator 150 is controlled by the control signal 156, which is generated by controller 146, so that the controller 146 can control the timing and/or phase of the charge pulse signal that is applied to the fluid stream 114. In this manner, the controller 146 can adjust both the droplet separation point 116 and the timing of the charge pulse signal from charge pulse generator 150, so that the charge pulse signal is applied at the proper time to optimize the charge on the droplets in droplet stream 122.

As further illustrated in FIG. 1, a positive and negative DC charge is applied to deflection plates 124, 126 during operation of the flow cytometer illustrated in FIG. 1. The positive and negative charges that are applied to deflection plates 124, 126 create a DC electric field that causes the charged droplets in droplet stream 122 to deflect and drop, by initial velocity and gravity, into separate deflected droplet streams 128, 130, depending upon the positive or negative charge on the droplet. Droplets that are not charged form non-deflected droplet stream 132, which fall directly into the waste collector 140. A conductive mesh 134 is placed over the collectors 138, 140, 142. When the droplets from the deflected droplet streams 128, 130 and the non-deflected droplet stream 132, that contain a charge, impinge on the conductive mesh 134, the charge of the droplets is transferred to the conductive mesh 134. The conductive mesh accumulates the charges from the droplets over a predetermined short period of time prior to dissipating. The conductive mesh 134 is connected by wire 136 to an electrometer 144 that detects the accumulated charge on the conductive mesh 134. The electrometer 144 generates an output signal that is transmitted to the controller 146 indicating the accumulated charge on the conductive mesh 134 for a predetermined period. The output of the electrometer 144 indicates the magnitude of the accumulated charge on the conductive mesh 134 for the accumulated period. In this manner, the controller 146 can determine the amount of charge on a predetermined number of droplets that intersect with conductive mesh 134 over the predetermined period, which is indicative of whether the droplets are being properly charged. The controller 146 can then be programmed to automatically change the timing and/or phase of the charge pulse generator 150 and/or the operational parameters of the piezoelectric voltage generator 152. At the same time, the controller can adjust strobe 120 using control signal 178, so that the camera 118 can obtain an image of the stream at the instant when the charge pulse is applied to the nozzle 102, which is displayed on display 148. The manner in which the controller 146 is programmed is more fully disclosed in the flow diagram illustrated in FIG. 6.

Figure 2:
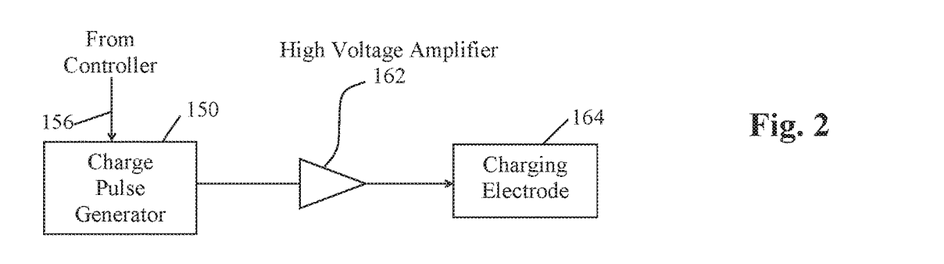
FIG. 2 is a schematic block diagram of an embodiment of a charge pulse circuit that can be utilized in the embodiment illustrated n FIG. 1.

FIG. 2 is a schematic block diagram of the charge pulse generator 150. As illustrated in FIG. 2, the charge pulse generator 150 receives a control signal 156 from the controller 146 (FIG. 1). Upon receipt of the control signal 156, the charge pulse generator 150 generates a charge pulse which is applied to a high voltage amplifier 162. The high voltage amplifier 162 is designed to provide a quick response and generate a narrow charging pulse that is applied to the charging electrode 164 that is located in the nozzle 102 (FIG. 1). The rise time of the charging pulse is very steep and the duration of the pulse is narrow, so that the charging pulse can be applied in a narrow timeframe, just before a droplet separates from the fluid stream 114, as illustrated in FIG. 1.

Figure 3A:
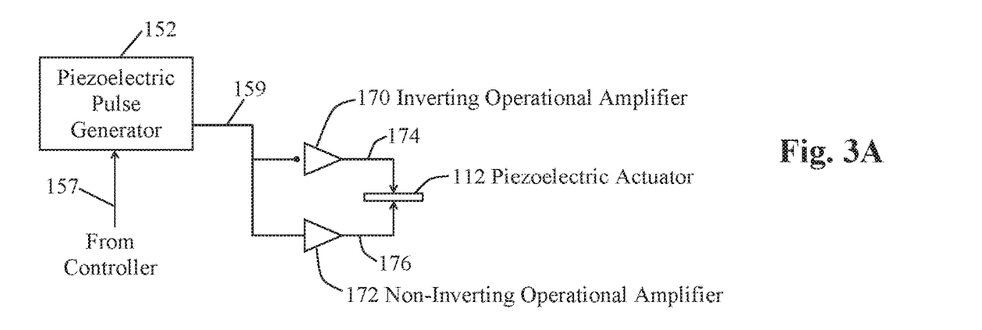
FIG. 3A is a schematic block diagram of an embodiment of a piezoelectric voltage generator circuit.

FIG. 3A is a schematic block diagram of the piezoelectric voltage generator circuit. The piezoelectric voltage generator 152 receives a control signal 157 from the controller 146. Upon receiving the control signal 157 from the controller 146, the piezoelectric voltage generator 152 generates an output 159 that is applied to inverting operational amplifier 170 and non-inverting operational amplifier 172. The inverted voltage 174 is applied to one side of the piezoelectric actuator 112 and the non-inverted voltage 176 is applied to another side of the piezoelectric actuator 112. In this manner, the piezoelectric actuator vibrates in accordance with the frequency and magnitude of the application of the inverted voltage 174 and the non-inverted voltage 176.

Figure 3B:
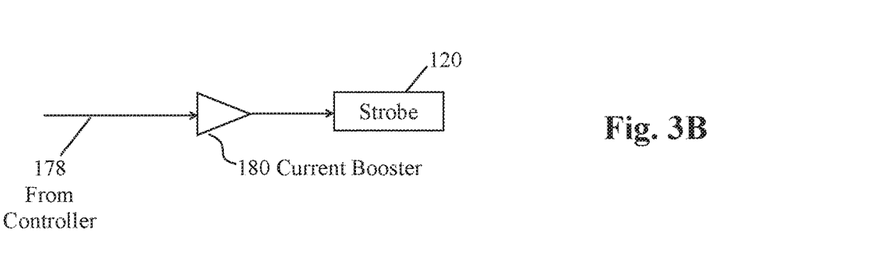
FIG. 3B is a schematic illustration of a strobe circuit.

FIG. 3B is a schematic illustration of the strobe circuit. As illustrated in FIG. 3B, a control signal 178 is received by the current booster circuit 180 from the controller 146. The current booster 180 boosts the control signal 178 from controller 146 and applies a current boosted signal 182 to the strobe 120. Upon receipt of the current boosted signal 182 from the current booster 180, strobe 120 emits a light signal that illuminates the fluid stream 114 at the droplet separation point 116.

Figure 4:
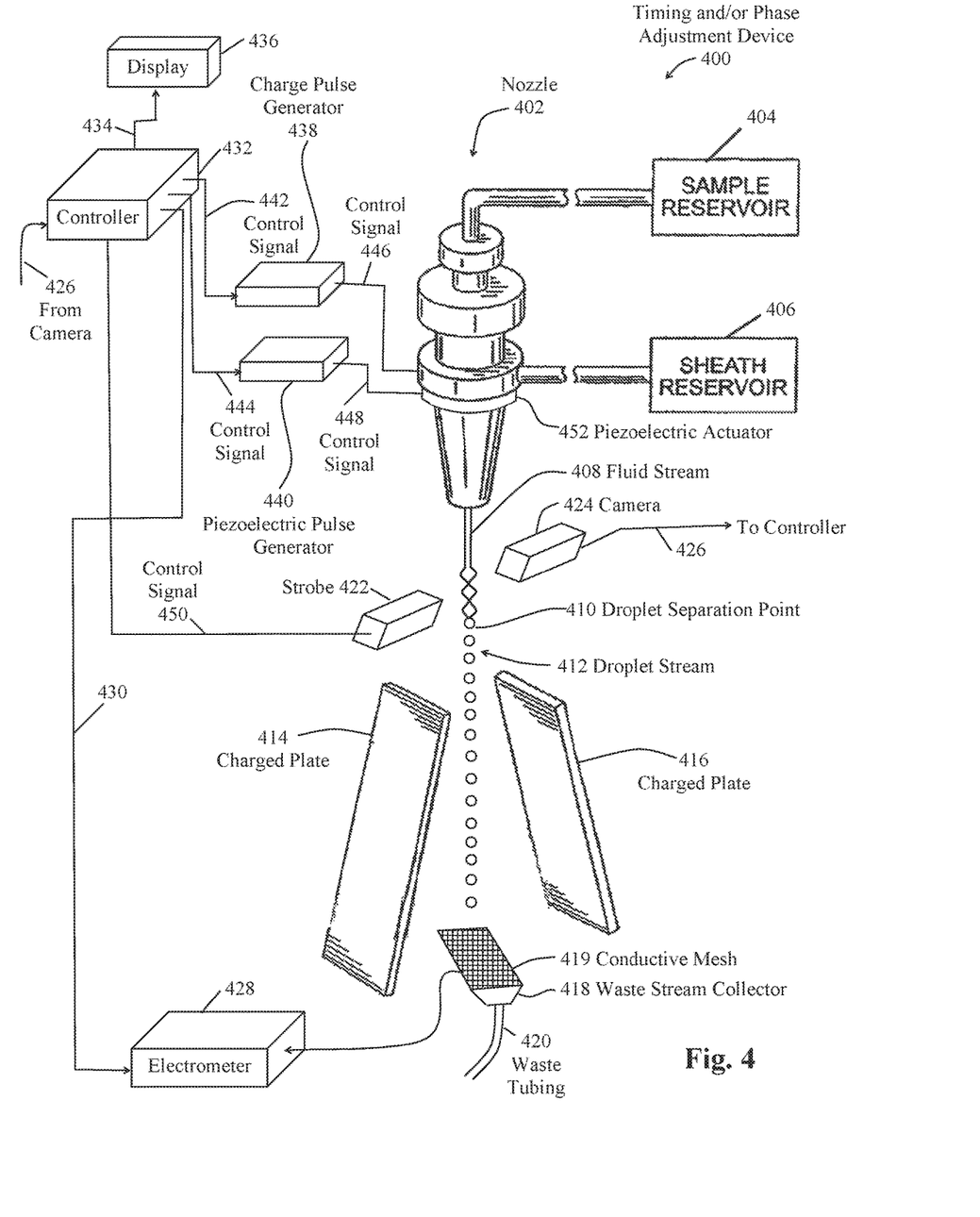
FIG. 4 is an isometric view of another embodiment of the invention.

FIG. 4 is schematic diagram of a timing and/or phase adjustment device 400. As illustrated in FIG. 4, nozzle 402 is coupled to the sample reservoir 404 and the sheath reservoir 406. Sample reservoir 404 provides the sample particles, while the sheath reservoir 406 provides the sheath fluid. Nozzle 402 generates a fluid stream 408 that includes the sample from the sample reservoir 404 and the sheath fluid from sheath reservoir 406. At start-up, and during other periods, the nozzle 402 may operate with just the sheath fluid from the sheath reservoir and not include sample particles from the sample reservoir 404. In either case, the fluid stream is created through a needle at the bottom of the nozzle 402. The fluid stream flows in a downward direction to a droplet separation point 410. At the droplet separation point, the fluid stream 408 separates into individual droplets. The piezoelectric actuator 452 causes a vibration in the fluid stream 408, which, in turn, causes the fluid stream to break into a droplet stream 412 at the droplet separation point 410. Variation of the signal on the piezoelectric actuator 452 can cause changes in the vibration of the piezoelectric actuator 452 which, in turn, can cause a change in the location of the droplet separation point 410. In addition, a change in the pressure of the sheath fluid from the sheath reservoir 406 can also change the location of the droplet separation point 410. For that reason, the pressure of the sheath fluid from the sheath reservoir 406 must be maintained in a highly accurate manner, such as disclosed in U.S. patent application Ser. No. 13/918,156, filed Jun. 14, 2013, entitled "Flow Rate Balanced, Dynamically Adjustable Sheath Delivery System for Flow Cytometry," which is specifically incorporated herein by reference for all that it discloses and teaches.

As also illustrated in FIG. 4, strobe 422 is located next to the fluid stream 408 and adjacent to the droplet separation point 410. Camera 424 is aligned to generate an image of the fluid stream 408 at the droplet separation point 410. Upon the flash of strobe 422, an image signal 426 is generated that is transmitted to the controller 432. Strobe 422 is operated by a control signal 450 from controller 432. The timing of the strobe allows the camera 424 to capture images at the droplet separation point 410, and other points that are above and below droplet separation point 410, so a user can view the fluid stream 408 just before, during and after the droplets of droplet stream 412 separate from the fluid stream 408, by simply adjusting the timing of the strobe 422. Once the droplet stream 412 is created, it passes between the charged plates 414, 416. During operation of the flow cytometer, a DC electric field is set up between the charged plates 414, 416. Droplets in the droplet stream 412 that are charged are then deflected in the electric field. During start-up and calibration of the timing and/or phase adjustment device 400, no charge is applied to the charged plates 414, 416 and the droplet stream 412 falls downwardly without deflection, as illustrated in the embodiment of FIG. 4, even though the droplets in the droplet stream 412 may be charged. The charged droplets in the droplet stream 412 fall downwardly to the waste stream collector 418 and out through waste tubing 420 for disposal. The waste stream collector 418 has a conductive mesh 419 that at least partially covers the opening in the waste stream collector 418. The conductive mesh can be a thin wire mesh, such as a copper mesh, constructed from thin copper wire, such as 22 gauge wire or smaller. A conductor 421 is conductively connected to the conductive mesh 419. The charge from the charge droplets is accumulated on the conductive mesh as more droplets intersect with the conductive mesh. The electrometer 428 reads the accumulated charge on the conductive mesh 419 and generates an output signal 430 that is applied to the controller 432, which is representative of the accumulated charge. The output signal 430 indicates the magnitude of the charge accumulated on the conductive mesh 419 and detected by the electrometer 428.

As also shown in FIG. 4, controller 432 reads the signal 430 that is representative of the magnitude of the accumulated charge and records that magnitude of the accumulated electrical charge from the conductive mesh 419. Charge pulse generator 438 and piezoelectric voltage generator 440 are also connected to the controller 432. Controller 432 generates a control signal 442 that is applied to charge pulse generator 440. In response, charge pulse generator 438 generates a series of charge pulse signals 446 that are applied to the fluid stream 408 through the nozzle 402. The sheath fluid in the fluid stream 408 is conductive since it contains free ions as a result of the dissolved salts that are present in the sheath fluid. Again, it is desirable to apply the charge pulse signals 446 to the fluid stream 408 during, but not after, the separation of the droplets from the fluid stream 408 at the droplet separation point 410. In this manner, the charges applied to the fluid stream 408 is transferred to droplets in the droplet stream 412. Accordingly, the timing and phase of the charge pulse signals 446 that are generated by the charge pulse generator 438, determine whether the droplet is fully charged. Again, if the charge pulse from the charge pulse generator 438 is applied too early, the charge on the fluid stream 408 may dissipate significantly before the droplet breaks away from the fluid stream 408. If the pulse is applied too late, the droplet will have no charge at all, since the droplet is not conductively connected to the fluid stream 408.

As also shown in FIG. 4, an image signal 426 is generated by the camera 424 and is applied to the controller 432. The controller 432 stores and transmits image signal 434 to the display 436. In this manner, a user of the system can view the image of the droplet as the droplet breaks away from the fluid stream 408.

As also illustrated in FIG. 4, piezoelectric voltage generator 440 receives a control signal 444 from controller 432. In response to the control signal 444, piezoelectric voltage generator 440 generates a piezoelectric actuator signal 448 that is applied to the piezoelectric actuator 452. The piezoelectric actuator signal 448 controls the magnitude and frequency of the operation of the piezoelectric actuator 452. Variation of the frequency and magnitude of the vibrations of the piezoelectric actuator 452, in response to the piezoelectric actuator signal 448, causes variations in the drop time and the location of the droplet separation point 410. In this manner, the location of the droplet separation point 410, as well as the phase of the separation of the droplet, can be varied by varying the piezoelectric control signal 444 from controller 432.

Figure 5:
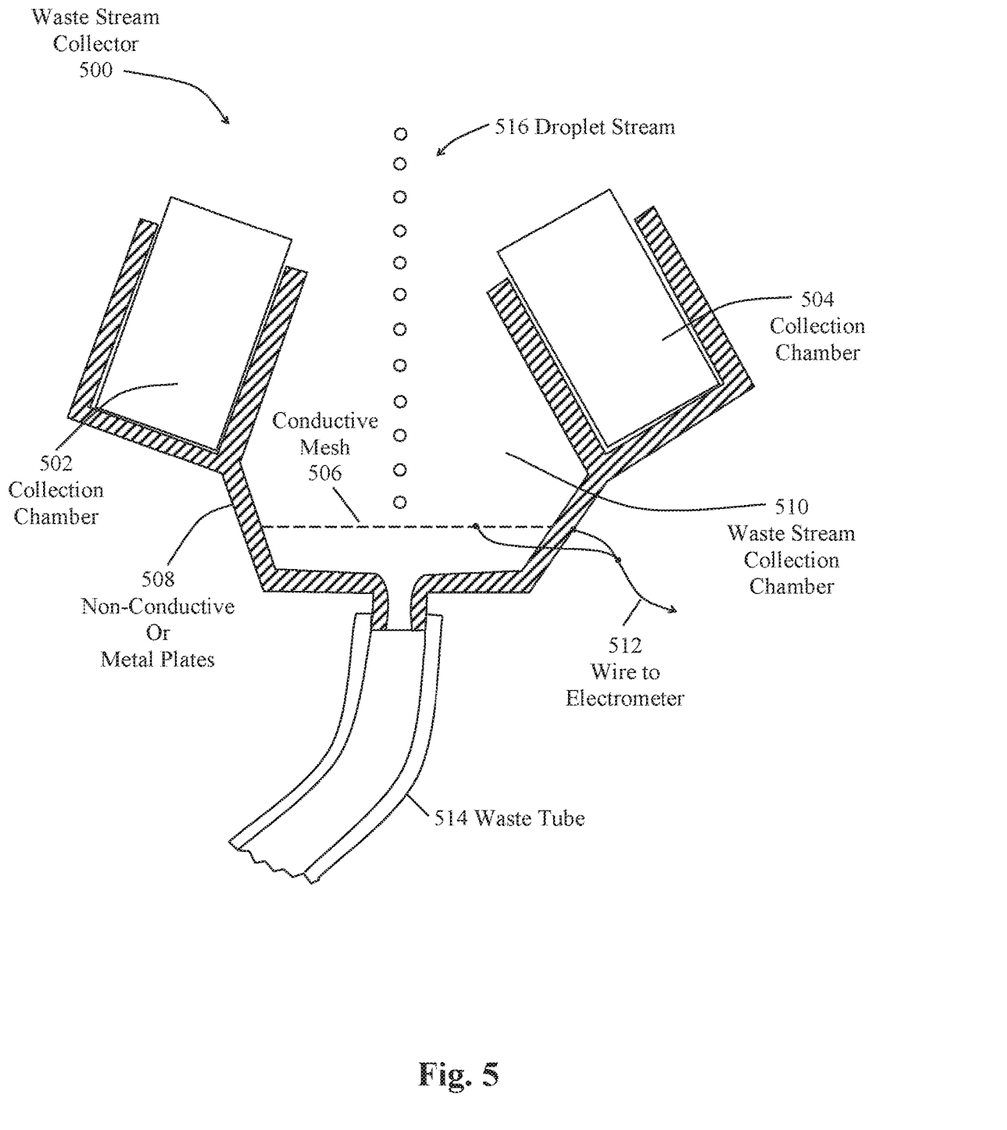
FIG. 5 is a work flow diagram illustrating the various processes performed by the controller of the various embodiments of the invention.

FIG. 5 is a cross-sectional diagram of an embodiment of a waste stream collector 500. Waste stream collector 500 can be utilized in the embodiment of FIG. 4 to collect charges from the charged droplets in the droplet stream 516. As indicated above with respect to FIG. 4, the charged plates 414, 416 are not charged, so the charged droplets of the droplet stream 516 are not deflected. The process of calibrating and adjusting the phase and location of the separation may occur during a start-up scenario or between running samples when the charged plates 414, 416 are not charged. The system may simply run a fluid stream of sheath fluid to generate the droplet stream 516. The droplet stream 516 may also include sample beads that simulate the sample to ensure that the droplets are properly formed. In that regard, the charged droplets in the droplet stream 516 fall into the waste stream collector cavity 510 and impinge on a conductive mesh 506. The collection chambers 502, 504 form the waste stream collection cavity 510 in the waste stream collector 500 that prevents the droplets in the droplet stream 516 from splashing and entering the collection chambers 502, 504. The conductive mesh 506 may be located in various positions within the waste stream collector cavity 510 to ensure that the charged droplets intersect with the conductive mesh 506. For example, the conductive mesh 506 may be disposed at a location that is higher in the waste stream collector 500 to ensure that the charged droplets in the droplet stream 516 initially intersect the conductive mesh 506, rather than other portions of waste stream collector cavity 510. The conductive mesh 506 may be mounted on metal plates 508, so that if the charged droplets in the droplet stream 516 break apart upon impact with the conductive mesh 506, the charge can be collected on the metal plates 508. In that case, the wire 512 can be connected to both the conductive mesh 506 and the metal plates 508, as illustrated in FIG. 5. Alternatively, the metal plates 508 may be a non-conductive material, such as plastic, so that charge is not dissipated into a larger metal surface. In that case, the wire 512 would simply be connected to the conductive mesh 506. The charged droplets from the droplet stream 516 then deposit charge onto the conductive mesh 506 and pass down through the waste tube 514. The collection chambers 502, 504 do not collect any of the charged droplets in the droplet stream 516, since the deflection plates are not activated to deflect the charged droplets. A number of charged droplets may be required to accumulate a sufficient charge on the conductive mesh 506 that can be detected via wire 512 by the electrometer. During setup, the timing and/or phase adjustment device 100, 400 may be operated for a specific period of time for a first series of setting, and then the setting changed and operated for a second equal period of time, so that the charges during these periods can be compared.

Figure 6:
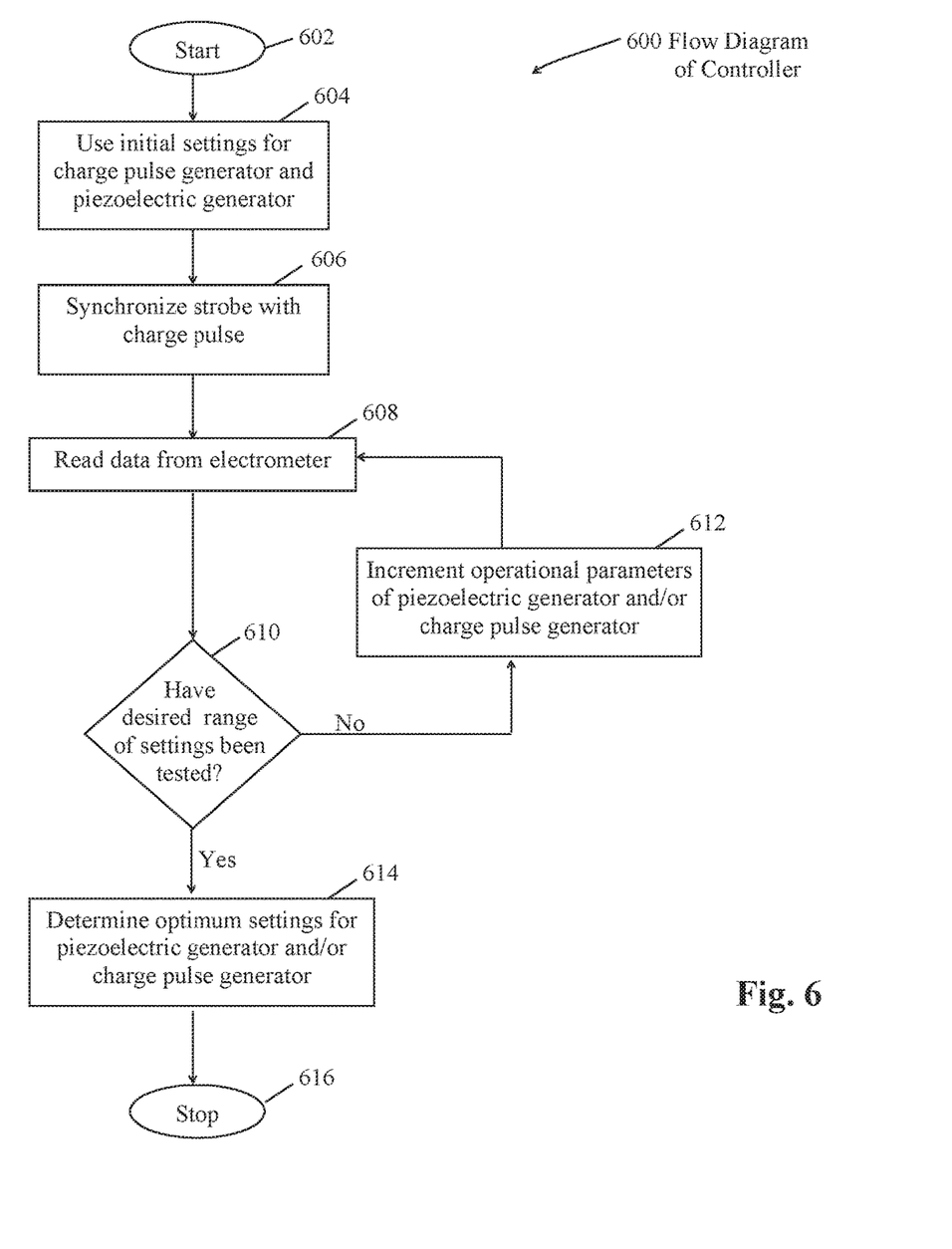
FIG. 6 is a flow diagram illustrating the operation of the controllers.

FIG. 6 is a flow diagram illustrating the operation of the controllers 158, 432 of the embodiments 100, 400 disclosed herein. At step 602, the process is initiated. At step 604, the controller uses initial settings for the charge pulse generator and piezoelectric generator. These settings may be the last settings that were used, or may be standard settings derived from averages of previous settings of the device. Alternatively, the settings may be at the end of the range of operation of these devices so that the devices can be incremented through the entire range, or a smaller range, of operation. At step 606, the operation of the strobe is synchronized with the charge pulse generated by the charge pulse generator. At step 608, the data is read by the controller from the electrometer. In that regard, the magnitude of the collected charge pulse is read and stored for the initial settings of the charge pulse generator and the piezoelectric generator. At step 610, it is determined whether the desired range of settings has been tested. In other words, the initial settings may be at one end of the operating range of the devices and the settings can then be varied to test the entire range of settings of the piezoelectric generator and/or charge pulse generator, so that results can be obtained for the entire range. Alternatively, a narrower set of test parameters can be utilized for selection of an optimal setting of the timing and phase adjustment. If the desired number of settings has not been utilized in the calibration procedure, the process proceeds to step 612, where the settings are changed. At step 612, the operating parameters of the piezoelectric generator and/or the charge pulse generator are incremented. In that regard, the piezoelectric generator can be adjusted individually to modify the phase. Alternatively, the timing and/or phase of the charge pulse generator can be changed individually to modify the time at which the stream is charged. In addition, both the piezoelectric generator and the charge pulse generator can be adjusted simultaneously to adjust both the phase and timing of the charge pulse. If it is determined at step 610 that the desired range of settings has been tested, the process proceeds to step 614. At step 614, the controller determines the optimum settings for the piezoelectric generator and/or the charge pulse generator based upon the maximum charge detected by the electrometer. At step 616, the process is completed.

Hence, the various embodiments disclose an automated way of obtaining an optimum timing and phase of the separation of the droplet from the fluid stream 408 based upon the collected charges of the charged droplets.

Figure 7:
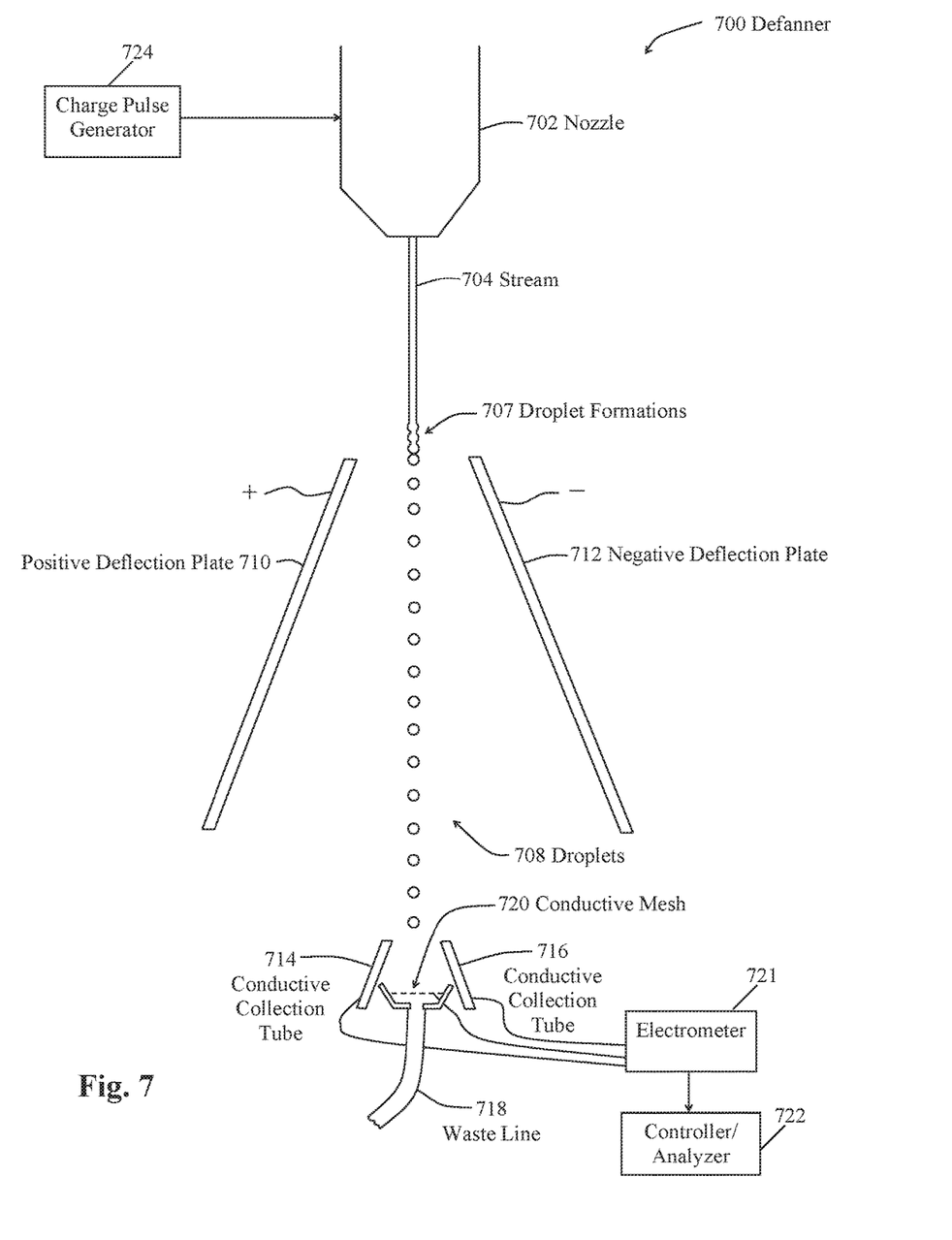
FIG. 7 is a schematic diagram of an embodiment of a defanner.

FIG. 7 is a schematic diagram of an embodiment of a defanner 700 that adjusts the amplitude of the charge pulses generated by the charge pulse generator 724 to compensate for variation in the charge of the droplets, such as droplet 706 that is about to be separated from stream 704, that has an induced charge from an electric field of one or more previously separated droplets 708, as described below with respect to FIG. 8.

As illustrated in FIG. 7, the nozzle 702 produces a fluid stream 704. The fluid stream 704 is vibrated by a piezoelectric actuator, as disclosed above with respect to FIG. 1, so that droplet formations, such as droplet formations 707, are created in the fluid stream 704, which results in droplets breaking off from the fluid stream 704. Just before droplet 706 separates from the stream 704, the charge pulse generator 724 generates a charge in the fluid stream 704, so that when a droplet separates from the fluid stream 704, the droplet is charged. The amount of the charge on each of the droplets is determined primarily by the amplitude of the charge pulse generated by the charge pulse generator 724. Positive deflection plate 710 and negative deflection plate 712 cause the charged droplets to deflect in a left or right direction, as illustrated in FIG. 7. The amount of the charge on the charged particle, as well as the voltages on the positive deflection plate 710 and negative deflection plate 712, control the amount of deflection of the droplet 708.

It is desirable to have a uniform amplitude of the charges on each of the droplets 708, so that each of the droplets is deflected by the same amount when passing through the static electric field generated by the positive deflection plate 710 and negative deflection plate 712. The defanning process, as disclosed herein, allows the alteration of the amplitude of the charge pulse generated by the charge pulse generator 710 to create uniform charges in each of the droplets 708.

As also illustrated in FIG. 7, deflected, charged droplets are collected by conductive collection tube 714 and conductive collection tube 716. Nominally uncharged particles pass through the conductive mesh 720 and are disposed in waste line 718. A uniform charge on each of the droplets 708 ensures that the deflected droplet streams are uniformly centered with the conductive collection tube 714 and conductive collection tube 716, which may have somewhat small openings. In this manner, the deflected droplets do not miss, or partially miss, or splash in the conductive collection tubes 714, 716.

As further illustrated in FIG. 7, the conductive collection tube 714, the conductive mesh 720, and the conductive collection tube 716 are all connected to electrometer 721. The electrometer 721 can precisely measure the charge on each of the conductive collection tubes 714, 716 and the conductive mesh 720. Electrometer 721 is a highly precise measuring device that can measure the charge on each of the collection tubes 714, 716 and wire mesh 720 with high precision. During calibration of defanner 700, the charges on each of these devices is transmitted to the controller/analyzer 722, which analyzes the charge information and stores calibration information for various series of charge pulses. In this manner, the controller/analyzer 722 can generate a control signal to control the charge pulse generator 724 to alter the charge pulse amplitude during operation of defanner 700.

Figure 8:
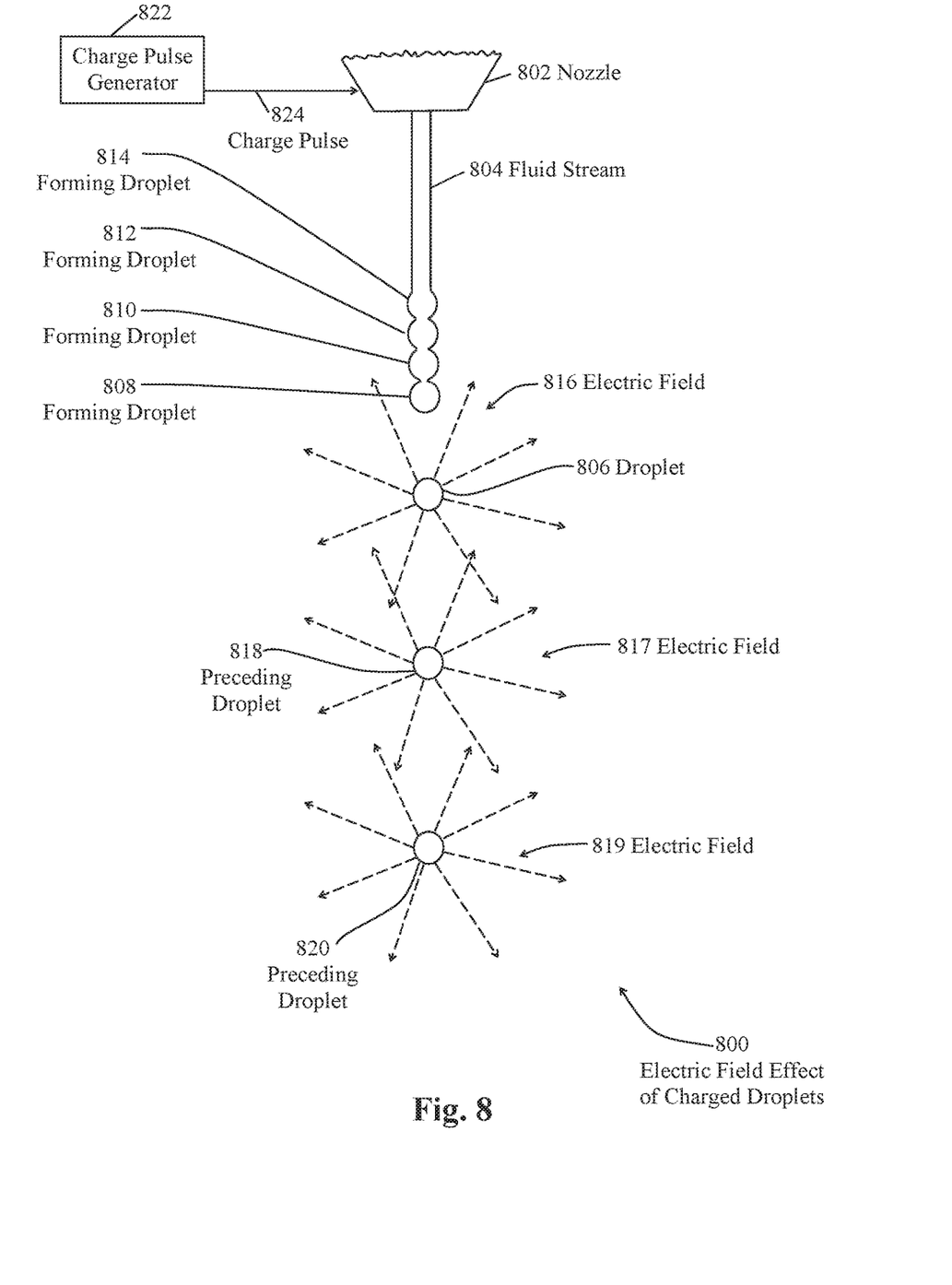
FIG. 8 is a schematic diagram illustrating the electric field effect of the charged droplets illustrated in FIG. 7.

FIG. 8 is a schematic diagram illustrating the electric field effect 800 of the charged droplets. As illustrated in FIG. 8, droplet 806 has recently separated from the fluid stream 804. Droplet 806 has a positive charge since the fluid stream 804 was positively charged by a charge pulse from charge pulse generator 818 just prior to the droplet 806 being separated from the fluid stream 804. The positive charge on the droplet 806 creates an electric field 816 that projects outwardly from the droplet 806. Typically, the droplet 806 reaches a maximum separation from the fluid stream of approximately 500 microns. The positive charge on the droplet 806 is sufficiently high and the separation distance between the droplet 806 and the last forming droplet 808 connected to the fluid stream 804 is sufficiently small that the electric field 816 has an effect on ions in the fluid stream 804. Of course, droplet 806 is extremely close to the fluid stream 804 and the forming droplet 808 just after droplet 806 separates from the fluid stream 804. The distance between the droplet 806 and the forming droplet 808 increases over time until the maximum separation of 500 microns, as indicated above, is reached. Of course, the closer that the droplet 806 is to the fluid stream 804, the greater the effect of the electric field 816 on the ions in the fluid stream 804, since the strength of the electric field 816 decreases approximately quadratically with distance. If the droplets were formed as a perfect sphere, the electric field would decrease as $1/r^2$ where r is the distance from the source of the electric field. However, the droplets are often formed with the presence of satellite droplets that join with the main droplets after separation from the fluid stream 804. The satellite droplet will carry its own amount of charge. Also, both the main and satellite droplets, regardless of their charge, will have an effect on the electric field radiating from other main and satellite droplets. Additionally, the main and satellite droplets are not perfect spheres. As such, the $1/r^2$ decrease of the electric field 816 is a very rough approximation.

The fluid stream 804, illustrated in FIG. 8, is a saline solution that has both positive and negative ions. Since the droplet 806 has a positive charge, the electric field 816 repels positive ions and attracts negative ions in the lower portion of the fluid stream 804, such as in forming droplet 808, and to a lesser extent in forming droplets 810, 812, 814. Of course, since the electric field 816 decreases quadratically with distance, the repulsion and attraction in forming droplet 808 is the strongest and falls off quadratically in each adjacent forming droplet 810, 812, 814. In one example, if forming droplet 808 is not scheduled to be charged with either a positive or a negative charge, but is to remain neutral, when forming droplet 808 separates from the stream 804, it will have a slightly negative charge, since negative ions in the fluid stream 804 migrate to forming droplet 808 and positive ions in fluid stream 804 migrate away from forming droplet 808 because of the electric field 816 generated by the droplet 806. The same is true for droplet 810, but to a lesser extent, since the positively charged droplet 806 is farther away from droplet 810 when droplet 810 is ready to separate from the fluid stream 804. In other words, droplet 806 will be another 500 microns from droplet 812 when droplet 812 is ready to separate from the fluid stream 804. As such, the electric field 816 generated by the droplet 806 has much less of an effect on forming droplet 810 when forming droplet 810 is ready to separate from stream 804, since the electric field 816 falls off quadratically with distance.

Accordingly, charged droplets that have separated from the fluid stream 804 can have an effect on forming droplets, such as forming droplet 808, that are about to separate from the fluid stream 804, as well as a quadratically reduced effect on the other forming droplets 810, 812, 814, just prior to separating from the fluid stream 804.

In the example given above, the positive charge on droplet 806 causes forming droplet 808 to be slightly more negative than forming droplet 808 would be if electric field 816 did not exist. This is true whether or not forming droplet 808 is charged (neutral), or if forming droplet 808 is charged negatively or positively. The same is true for the effect of preceding droplet 818 on forming droplet 808. If one or more preceding droplets, that precede droplet 806, such as preceding droplets 818, 820, have a positive charge, the electric fields 817, 819 from droplets 818, 820, respectively, will add to the electric field 816 to further affect droplets 808, 810, 812, 814. If preceding droplets 818, 820 have a negative charge, the electric fields 817, 819 from droplets 818, 820, respectively, would subtract from the positive electric field 816. The effects of one or more electric fields from separated droplets will therefore alter the charge on each newly separated droplet. As such, the history of the charges on the droplets is relevant in determining the magnitude of the charge pulse 824 to be generated.

In order to detect the effect of one or more electric fields from droplets that have separated from the fluid beam, the embodiment of FIG. 7 can be used to directly measure the charges on both the intentionally charged droplets and the neutral droplets in droplet stream 708. Conductive collection tube 714 is connected to the electrometer 721 and collects negatively charged droplets. In contrast, droplets in droplet stream 708, that have been intentionally positively charged, are collected in conductive collection tube 716. Of course, if the direction of the deflection electric field is reversed, then the polarity of the charge collected in the tube will also be reversed. Droplets in droplet stream 708, that have not been intentionally charged, are collected by the conductive mesh 720. Since it is difficult to measure the individual charges on individual droplets, the charges from a series of droplets can be collected and averaged over the number of droplets to determine the charge on individual droplets. In order to obtain accurate data, the droplets must be created under similar conditions. In the example illustrated in FIG. 8, droplet 806 may be an intentionally positively charged droplet, while preceding droplets 818, 820 are neutral droplets. Forming droplet 808 may be negatively charged. This series can be repeated a number of times to accumulate a number of charges, so that the electrometer 721 can record a charge that can be averaged over a number of particles. In the present example, the charge on the conductive collection tube 714, is the accumulation of the negative charges from a plurality of forming droplets, such as forming droplet 808. The total charge can then be divided by the total number of droplets to obtain an average charge per droplet of each of the forming droplets 808.

As explained above, the forming droplet 808 has been influenced by the electric field 816, so that the negative charge on forming droplet 808 will be slightly more negative than the charge it would have from the charge pulse 824 because of the induced negative charge from electric field 816. In this manner, the influence of the electric field 816 on the forming droplet 808 can be determined and isolated. This same process can be used to determine the influence of the electric field 817 from preceding droplet 818 on forming droplet 808 if preceding droplet 818 is charged. In this scenario, preceding droplet 818 may be positively charged and droplet 806 and preceding droplet 820 are nominally neutral, i.e., not charged by charge pulse 824. In that case, electric field 816 and electric field 819, to the first order, do not exist. The electric field 817 may then have some effect on the forming droplet 808. Again, assuming the preceding droplet 818 is positively charged, the electric field 817 will cause negative ions to migrate toward the bottom of the fluid stream 804 and into the forming droplet 808, while positive ions in the fluid stream 804 will be repelled and move away from the forming droplet 808. This will cause forming droplet 808 to be slightly more negatively charged because of the effects of the electric field 817. Forming droplet 808 can then be charged negatively, just prior to separation, by charge pulse 824, so that forming droplet 810 can be collected in conductive collection tube 714 and isolated from the effects of other fields. Again, a series of droplets can be charged in this manner and the result of the conductive charge on the conductive collection tube 714 can be averaged to determine the effect of the electric field 816 from droplet 806 on forming droplet 810.

Various combinations of charges can be utilized, as desired, to analyze the effect of electric fields from droplet 806 and preceding droplets 818, 820 on the forming droplet 808. Once the effect of these electric fields is determined by a controller/analyzer 722, the controller/analyzer 722 can adjust the amplitude of the charge pulse generated by the charge pulse generator 724 for each forming droplet 808, so that each of the droplets 806, that have separated from the stream 804, have a substantially uniform charge and are deflected by a substantially uniform amount by the static field of the positive deflection plate 710 and negative deflection plate 712. The process of adjusting the amplitude of the charge pulse for the various charge scenarios and combinations of charges that may exist on the droplets 708 can then be determined by controller/analyzer 722, which may be a processor or state machine.

This calibration process and analysis may be used periodically, such as during start-up of the system, so that the defanning process may be adjusted for various processing operations that may vary from day to day. In this manner, highly accurate calibration of the system can be achieved.

Figure 9:
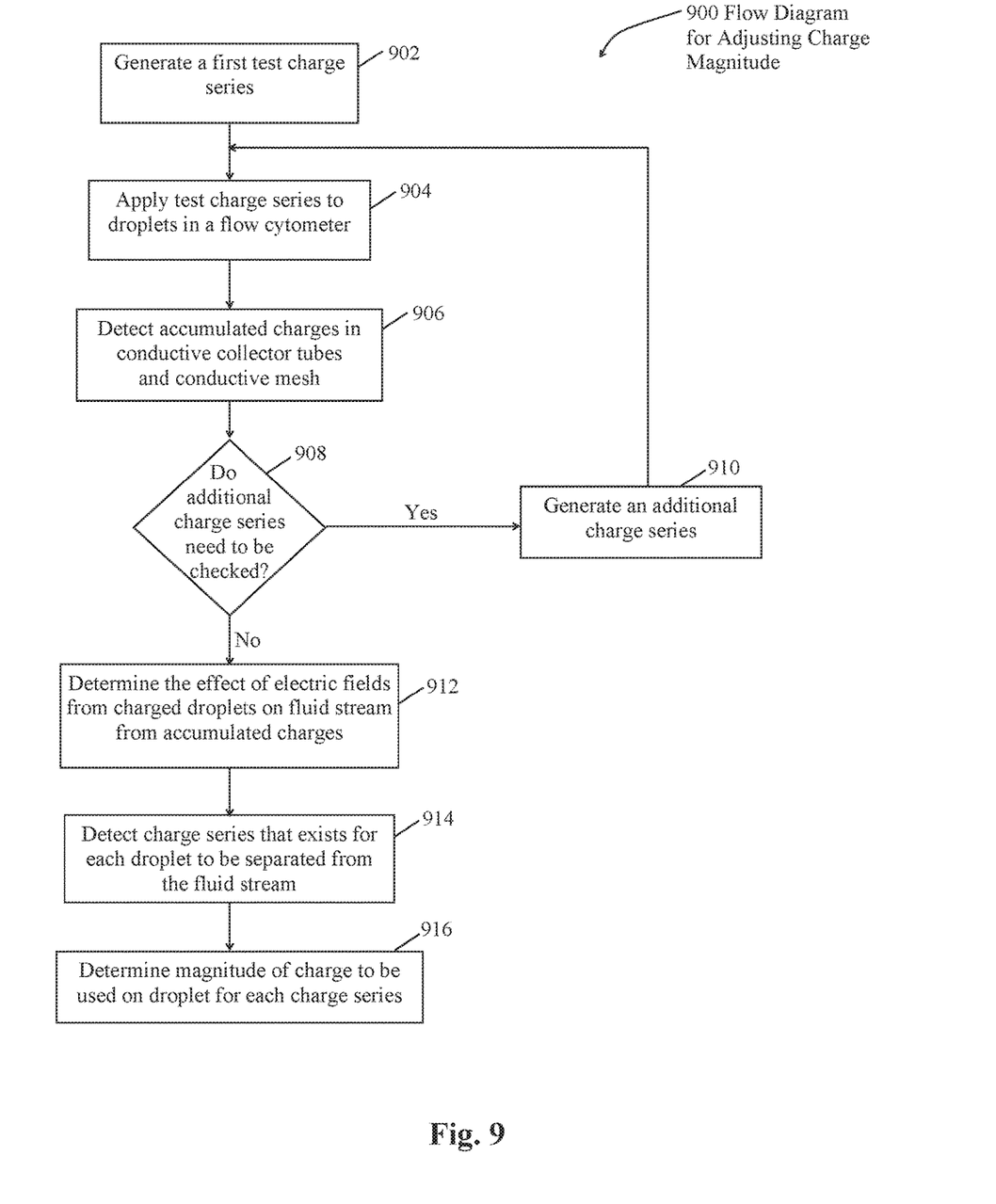
FIG. 9 is a flow diagram for adjusting the charge magnitude of the charge pulse generated by the charge pulse generator illustrated in FIG. 7.

FIG. 9 illustrates a flow diagram 900 for adjusting the charge magnitude of the charge pulse generated by charge pulse generator 724, illustrated in FIG. 7. As shown in FIG. 9, the process starts by generating a first test charge series 902. For example, a test charge series may comprise the generation of a positively charged droplet every fourth droplet. At step 904, as illustrated in FIG. 9, the test charge series is applied to droplets in a flow cytometer, such as illustrated in FIG. 8. At step 906, the accumulated charges in the conductive collector tubes 714, 716 and conductive mesh 720 are detected. In the example given above, in which every fourth particle is charged positively, a slightly negative charge will be accumulated on the conductive mesh 720 of the defanner 700. The slightly negative charge on the conductive mesh 720 is the result of the electric field 816 causing negative ions in fluid stream 804 to be attracted to the bottom portion of the fluid stream 804, so that the neutral forming droplet 808 is actually slightly negative once the forming droplet 808 separates from the fluid stream 804. A much lesser effect is created on forming droplet 808 from the electric field 817 of droplet 818 and a negligible, or non-existent, effect is created by electric field 819 of droplet 820 on forming droplet 808.

In another example, every fourth droplet, which is droplet 806, may be positively charged, while every fifth droplet, i.e., forming droplet 808, is negatively charged when separated from the fluid stream 804. In this scenario, the electric field 816 of droplet 806 will repel positive ions and attract negative ions in the fluid stream 804, so that the forming droplet 808, when it is separated from the fluid stream 804, will have a negative charge that is slightly more negative than the negative charge that forming droplet 808 would have without the influence of electric field 816. In this example, then, every fourth droplet is positively charged and every fifth droplet is negatively charged. The remaining droplets are neutral. The negatively charged forming droplet 808 is deflected into conductive collection tube 714 and is isolated from the neutral droplets and the positively charged droplet 806. By accumulating multiple negatively charged droplets in conductive collection tube 714, using this same charge series, the effect of the electric field 816 from droplet 806 or forming droplet 808 can be measured and isolated by measuring the additional negative charge of the negative droplets collected by conductive collection tube 714. In other words, the negatively charged droplets are isolated in conductive collection tube 714, and the effect of the electric field 816, on forming droplet 808, is isolated. This additional negative charge can be divided by the number of droplets to determine the extra charge on each individual negative droplet. In this manner, the effect of the electric field 816 from droplet 806 can be isolated and measured using this charge series.

Similarly, the effect of the electric field 817 on forming droplet 808 can be measured using a different charge series. For example, droplet 818 can be positively charged, while droplet 806 is not charged (neutral). Forming droplet 808 can be negatively charged just prior to separation. In this manner, forming droplet 808 can be separated from the other droplets and collected in conductive collection tube 714 to determine the effect of electric field 817 by measuring the charge in conductive collection tube 714. This process isolates the effect of electric field 817 on forming droplet 808 to determine an adjustment of the magnitude of the charge pulse 824 from the charge pulse generator 822. Droplet 806 and, to a much lesser extent, preceding droplet 818 are the only droplets that would have electric fields that could effectively influence the migration of ions in the fluid stream 804. Droplets, such as preceding droplet 820, has an electric field that is so small at the location of the forming droplet 808 that it will not measurably affect the ions in the fluid stream 804. The isolated effect of each of the electric field 816 and the electric field 817 allow a determination of the amount that the charge pulse 824 must be modified to achieve consistent charges on the droplets.

Figure 10:
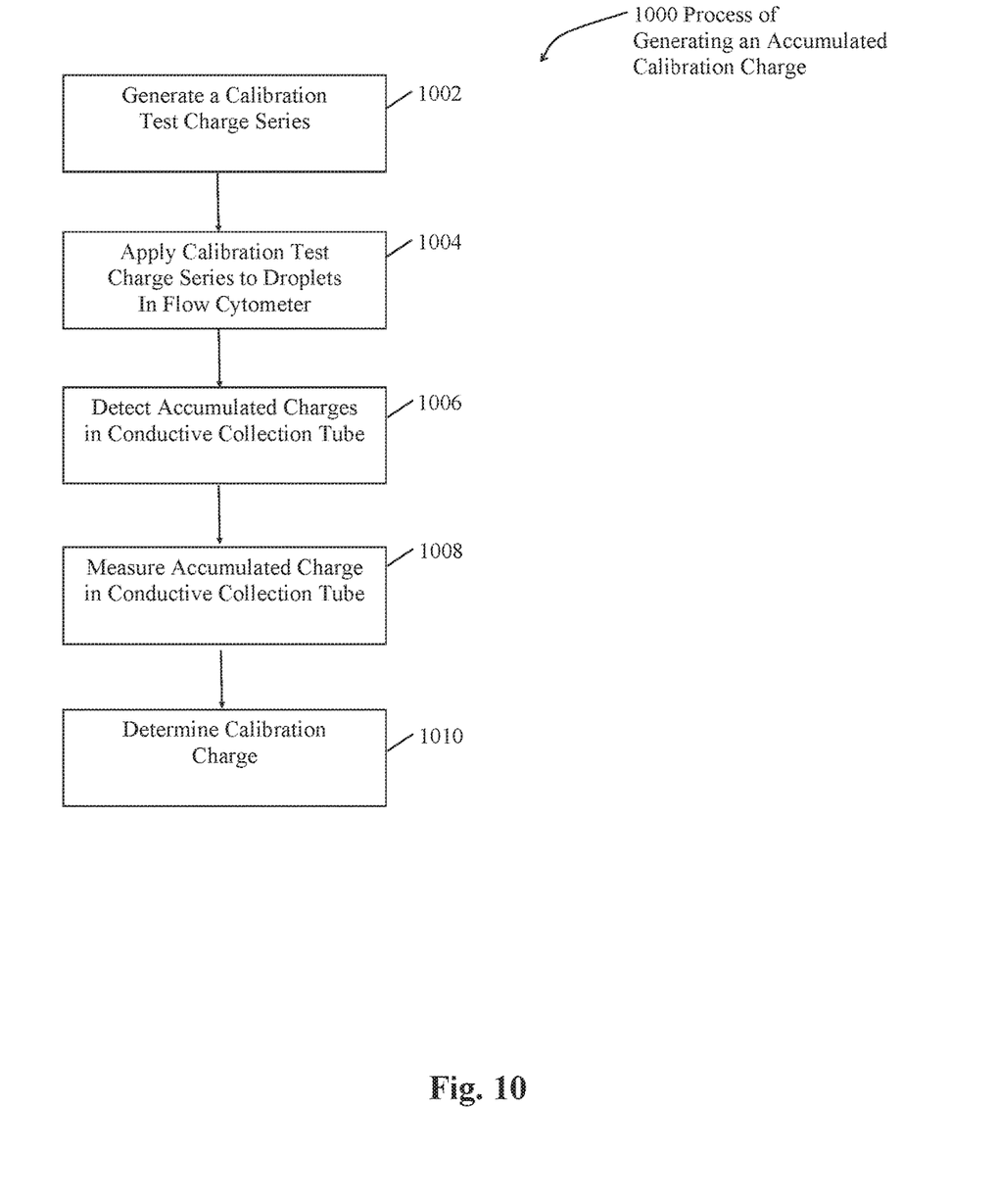
FIG. 10 is a flow diagram illustrating the process of generating an accumulated calibration charge.

At step 908 of FIG. 9, it is determined whether additional charge series need to be checked. If additional charge series need to be checked, an additional charge series is generated at step 910. The process then proceeds back to step 904, where the new charge series is applied to the droplets in the flow cytometer. If an additional charge series does not have to be checked, the process proceeds to step 912. At step 912, the effect of the electric field from the charged droplets on the fluid stream is determined from the measured accumulated charges in the conductive collection tubes 714, 716 and the conductive mesh 820. This process is explained in more detail above, in which the effects of one or more electric fields can be isolated by identify the effect of these electric fields on the droplets. The measured accumulated charged in the conductive collector tubes 714, 716 and conductive mesh 820 are compared with an accumulated charge from a calibration test charge series, which is explained in more detail below with respect to FIG. 10. In that regard, the measured accumulated charges of droplets that have been affected by electric fields is compared to an accumulated calibration charge to determine the magnitude of the charge that has affected the droplets that have been affected by electric fields from preceding droplets. FIG. 10 discloses the manner in which an accumulated calibration charge is generated.

At step 914 of FIG. 9, the system detects the charge series that exists for each droplet to be separated from the fluid stream. At step 916, the magnitude of the charge pulse 824 is determined for each droplet based upon the charge series. For example, if droplet 806 has a positive charge and preceding droplet 818 has a positive charge, the effect of the electric field 816 on forming droplet 808 is added to the effect of the electric field 817 of the preceding droplet 818 to determine the overall effect on the forming droplet 808. If the preceding droplet 818 is negatively charged and droplet 806 is positively charged, the effect of the electric field 817 of the preceding droplet 818 on forming droplet 808 is subtracted from the effect of the electric field 816 of positively charged droplet 806. In this manner, each charge series and the effect of the electric fields for each charge series based on the history of the charges on droplet 806 and the preceding droplets 818, 820, can be determined to create a charge pulse 824 that is modified to produce droplets that have a uniform charge and are deflected by a substantially uniform amount.

As described above, decision block 908 determines whether additional charge series need to be checked. One of those charge series may be the process 1000 that is disclosed in FIG. 10. In that regard, at step 912 of FIG. 9, a comparison is made of the accumulated charge of droplets, that have been affected by electric fields prior to separation from the fluid stream, with droplets that have not been substantially affected by electric fields, in the manner set forth above with respect to the description of step 912.

Referring again to FIG. 10, the process of generating an accumulated calibration charge begins with the generation of a calibration test charge series at step 1002. The calibration test charge series, at step 1002 of FIG. 10, may comprise the charging of every third, or fourth, or fifth, etc. droplet by a charge pulse, such as charge pulse 824, illustrated in FIG. 8. An example given above, in which droplet 806 is positively charged and forming droplet 808 is negatively charged, and accumulated in conductive collector tube 714, the calibration charge may be produced by a charge series in which every third, fourth, fifth, etc. droplet is negatively charged and accumulated in conductive collection tube 714. Whether the charged droplet in the charge calibration series is the third, fourth, fifth, etc. depends on the desired isolation of the forming droplet 808 from the electric fields of any of the preceding droplets. As indicated above, the electric field 819 normally does not have a measurable effect on the ions in the fluid stream 804. However, greater isolation may be desired so that the fourth, or fifth, or sixth, or etc. droplet in the charge series is charged to ensure that there is no effect from the electric field of the preceding droplet.

At step 1004 of FIG. 10, the calibration test charge series is then applied to the droplets in the flow cytometer, illustrated in FIG. 8. At step 1006, the charge in at least one of the conductive collection tubes 714, 716 is measured to provide an accumulated calibration charge. This accumulated calibration charge is then determined at step 1010 and may be used to compare with the accumulated charge that is run during the calibration process.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of adjusting the timing or phase of a charge pulse signal for charging droplets from a fluid stream of sheath fluid in a flow cytometer, the method comprising:
   forming a fluid stream by flowing the sheath fluid through a nozzle, wherein the fluid stream separates into droplets after exiting the nozzle;
   applying the charge pulse signal to the nozzle during a calibration phase, wherein each droplet that separates from the stream when the charge pulse signal causes a charge to be applied to the nozzle becomes a charged droplet and each droplet that separates from the stream when the charge pulse signal does not cause a charge to be applied to the nozzle remains an uncharged droplet;
   receiving the charged and uncharged droplets in a charge collector during the calibration phase;
   collecting charges during the calibration phase from the charged droplets for a plurality of timing or phase settings using an electrometer that is connected with the charge collector;
   measuring the charges collected from the charged droplets for each of the timing or phase settings to create a plurality of collected charged droplet signals that are each indicative of an accumulated charge signal produced by the electrometer;
   determining a collected charged droplet signal of the plurality of collected charged droplet signals that has the greatest magnitude; and
   operating the flow cytometer with a timing or phase setting of the plurality of timing or phase settings that corresponds to the collected charge droplet signal that has the greatest magnitude.

2. The method of claim 1, wherein the charge collector is a thin conductive mesh.

3. The method of claim 1, wherein the thin conductive mesh is disposed in a waste stream collector in the flow cytometer.

4. The method of claim 1, wherein
   the charge collector comprises metal surfaces of a droplet collector.

5. The method of claim 4 wherein the process of adjusting the timing or phase of the charge signal comprises adjusting the timing of the charge pulses in the charge pulse signal.

6. The method of claim 4 wherein the process of adjusting the timing or phase of the charge pulse signal comprises adjusting the phase of the charge pulse signal.

7. A method of adjusting the amplitude of a charge signal that is applied to droplets formed from a fluid stream in a flow cytometer to create a substantially uniform charge on the droplets in a fluid stream comprising:
   controlling a charge pulse signal to impart a positive charge, a negative charge, or a neutral charge to each droplet generated during a calibration phase to produce a plurality of calibration charge series, each calibration charge series including a sequence of droplets;
   subjecting each calibration charge series to an electric field to cause the droplets in that calibration charge series having a positive charge imparted to them by the charge pulse signal to be collected in a first conductive droplet collector, the droplets in that calibration charge series having a negative charge imparted to them by the charge pulse signal to be collected in a second conductive droplet collector, and the droplets in that calibration charge series having a neutral charge imparted to them by the charge pulse signal to be collected in a third conductive droplet collector;
   detecting accumulated charges in the first conductive collector, the second conductive collector, and the third conductive collector for one or more instances of each calibration charge series
   determining, for each calibration charge series and based on the accumulated charges for the first conductive collector for that calibration charge series, the accumulated charges for the second conductive collector for that calibration charge series, and the accumulated charges for the third conductive collector for that calibration charge series, an average measured charge magnitude for each droplet of that calibration charge series,
   adjusting an amplitude of the charge pulse signal used to impart positive, negative, or neutral charges to each droplet of a first charge series based on the average measured charge magnitude for droplets in the calibration charge series that corresponds with the first charge series.

8. The method of claim 7, further comprising:
   controlling the charge pulse signal to impart a droplet in one or more of the charge series with a charge polarity opposite the charge polarity of an adjacent preceding droplet in the one or more of the charge series.

9. The method of claim 8, wherein the process of detecting the accumulated charges comprises using an electrometer that measures the accumulated charge for each of the first conductive collector, the second conductive collector, and the third conductive collector.

10. The method of claim 7, further comprising:
    determining an amount by which the average measured charge magnitude for a droplet of a charge series differs from an expected average charge magnitude and modifying the charge pulse signal amplitude based on the amount.

11. The method of claim 7, further comprising:
    generating a first calibration charge series of the plurality of calibration charge series that includes charged droplets that are not affected by electric fields of other droplets in the first calibration charge series;
    collecting the charged droplets of the first calibration charge series in a conductive collector selected from the group consisting of: the first conductive collector and the second conductive collector;
    comparing the average measured charge magnitude of the charged droplets of the first calibration charge series with the average measured charge magnitude of similarly charged droplets in one or more other calibration charge series to obtain a charge variation amount;
    using the charge variation amount to adjust the amplitude of the charge signal.

12. A system for adjusting a charge amplitude of a charge pulse signal that is applied to droplets formed from a fluid stream in a flow cytometer to create a substantially uniform charge on said droplets comprising:
    a charge pulse generator that generates said charge pulse signal in response to a control signal, that has a charge magnitude that charges droplets just prior to separation from said fluid stream to obtain charged droplets;
    at least one conductive collector that collects said charged droplets and accumulates a charge having a charge magnitude;

an electrometer connected to said at least one conductive collector that detects said charge magnitude and generates a charge magnitude signal;

a processor that receives said charge magnitude signal and generates said control signal, said control signal producing a plurality of charge series of said droplets that produces affected droplets that have a charge that has been affected by electric fields of preceding droplets and non-affected droplets that have not been affected by electric fields of preceding droplets, and compares said charge magnitude signal for said affected droplets and said non-affected droplets for said plurality of charge series to alter said charge magnitude of said control signal, which charges said droplets to a uniform magnitude during operation of said flow cytometer.

* * * * *